United States Patent [19]
Schroeder

[11] 4,255,141
[45] Mar. 10, 1981

[54] METHOD FOR MARKING TIGHT DENTAL CASTING

[76] Inventor: Helmut H. Schroeder, 205 E. Third Ave., San Mateo, Calif. 94401

[21] Appl. No.: 74,710
[22] Filed: Sep. 12, 1979
[51] Int. Cl.$^3$ ............................................. A61C 0/00
[52] U.S. Cl. ........................................ 433/68; 433/71
[58] Field of Search .................. 433/68, 69, 70, 214, 433/71

[56] References Cited

U.S. PATENT DOCUMENTS

| | | | |
|---|---|---|---|
| 3,421,223 | 1/1969 | Stark | 433/70 |
| 3,604,116 | 9/1971 | Shpuntoff | 433/71 |
| 3,707,771 | 1/1973 | Guerra | 433/70 |
| 3,918,160 | 11/1975 | Friedman | 433/70 |
| 3,959,881 | 6/1976 | Kokal, Jr. | 433/70 |

FOREIGN PATENT DOCUMENTS 51-61611  5/1976  Japan ......................... 433/71

*Primary Examiner*—Robert Peshock
*Attorney, Agent, or Firm*—Townsend and Townsend

[57] ABSTRACT

A method for marking contact between a dental mounting such as a prepared tooth and a prosthetic device such as a crown, wherein the prosthetic device is to be modified to conform to the mounting. The method comprises applying a clear, mildly adhesive liquid to the surface of the mounting in a thin, uniform film, seating the thoroughly dried surface of the prosthetic device against the mounting to cause protruding areas to abut to one another and to transfer a residue of the liquid adhesive to the protruding areas of the surface of the prosthetic device, and then highlighting the residue on the prosthetic device surface by dusting with a visible powder which clings to the residue, and finally removing the excess powder whereby the areas of undesired protrusion on the surface of the prosthetic device are indicated. Thereafter, the protruding areas of the prosthetic device can be ground away, and the process can be repeated until undesired areas of contact can be eliminated. The method does not damage or modify the surface of the mounting.

4 Claims, No Drawings

METHOD FOR MARKING TIGHT DENTAL CASTING

BACKGROUND OF THE INVENTION

1. Field of the Invention

This invention relates generally to dentistry and more particularly to a method of indicating points of contact between the interior of a prosthetic crown or the like and a prepared tooth, a die, an abutment or like mounting.

It is the practice when fitting a crown to a prepared tooth or die to position the crown to a point of resistance. Due to imperfections in the molding process involved in making impressions, there may be undesired protrusions and irregularities in the surface of the prosthetic crown confronting its mounting. Ideally, a crown should not be tight but should fit snugly and uniformly to its mounting. There is therefore needed a technique for indicating undesired protruding areas in the crown surfaces so that they can be eliminated.

2. Description of the Prior Art

Systems are known for identifying areas of voids between a crown and a mounting. For example, there exists a system wherein a paste, applied to either the mounting or the crown, is displaced by insertion of the crown onto the mounting. Areas of protrusion are indicated by the lack of a paste at areas of contact between the crown and its mounting.

Another system for identifying seating problems is marketed under the brand name "Liqua-Mark" Counter Indicator, which is a liquid system for identifying counter-seating problems and high occlusions between teeth. The composition of the material appears to be a slurry of a colored powder and a liquid. It has been found that it is somewhat messy, time consuming to use and inaccurate in its marking ability when used as a crown seating indicator. Moreover, it is not recommended for use in the mouth because of the danger of ingestion of toxic materials.

Another common technique for crown seating indication is the use of a graphite pencil wherein the graphite is applied directly to the prepared tooth or die, pressed into the crown and transferred upon contact to the crown. This technique is also messy, and it tends to mark permanently and even damage the die.

What is needed is a method for indicating proper seating which is accurate, relatively clean, substantially non-toxic in the event of ingestion, and which does not cause damage.

SUMMARY OF THE INVENTION

The invention comprises application of a thin uniform film of a clear, non-toxic, mildly adhesive and readily removable liquid to a first dental surface, such as a tooth or die, abutting the first dental surface to a second, dry dental surface of a dental prosthetic to transfer to the second dental surface a residue of the liquid to points of occlusion between the first and second dental surfaces, and highlighting the points of undesired occlusion on the prosthetic dental surface by dusting the prosthetic dental surface with a colored powder which adheres to the residue. Undesired protrusions causing tight fit can thereafter be eliminated by grinding away highlighted points of occlusion on the second dental surface. The inventive technique quickly and accurately identifies undesired occlusions between a dental mounting and the interior of a dental prosthetic device. The technique according to the invention permits accurate selective elimination of undesired protrusions from the working surface which is generally within the interior of the prosthetic device. It is specifically intended that the mounting, such as a underlying tooth or its corresponding mold, not be modified in the process of fitting a crown or the like.

DETAILED DESCRIPTION OF SPECIFIC EMBODIMENTS

The first step according to the inventive technique is to apply a thin uniform film of a substantially clear non-toxic adhesive liquid to the first dental surface, such as the impression of a prepared tooth or the prepared tooth itself. The non-toxic adhesive liquid is preferably glycerin mixed about 10 to 1 with a non-toxic liquid laboratory soap, commonly known as Green Soap. A specific soap is made by Eli Lilly & Co. of Indianapolis, Indiana under the name NDC Lilly, Green Soap Tincture N.F. The glycerin has mild adhesive properties and the soap solution promotes a smooth, thin, even coating of the glycerin. It is been found that the glycerin and soap mixture has a tendency to separate, so it is important to shake the mixture well before application. The glycerin-soap mixture is applied directly to the first surface preferably by painting with a small brush. A spray may be used, but it is not preferred because the spray target is difficult to localize.

Excess liquid typically accumulates on portions of the first surface. The excess liquid can be removed by blowing with an air gun at moderate pressure, thereby leaving a thin, even film over the first surface.

The next step in the inventive process is the seating of the two surfaces, namely the seating of the working surfaces of a prosthetic device such as a dental crown onto the first surface or the mounting. The prosthetic device should be dry and clean to minimize false readings. The clean and dry prosthetic device is seated gently onto the painted mounting to a point of resistance in order to transfer a residue of the liquid to the points of occlusion between the first and second surfaces. Thereafter, the prosthetic device is removed from the mounting for subsequent processing. The mounting is not further involved and may be rinsed clean when convenient.

In order to more readily identify the points of occlusion as indicated by the transferred liquid residue, the points of occlusion are highlighted on the residue-marked surface of the prosthetic device by applying a dust of a colored powder. The powder is typically dusted by a fine brush or blown on the prosthetic device by a fluidizing applicator in sufficient quantity to cause adhesion between the liquid residue and the powder. The excess powder may be blown off of the prosthetic device with a mild air stream, leaving the powder only in the areas of residue adhesion. The powder application process may be carried out over a waste drawer to minimize waste and area contamination. Obvious colored markings on the prosthetic device, which are at the areas of residue adhesion, indicate areas of tight contact between the prosthetic device and the mounting.

The indicator powder may be a dry red food coloring dye or the like. To promote smoother flow of the red dye, talcum powder may be included in the mixture at a ratio of 1 to 3 parts talcum to 1 part dry dye. The toxicity of the powder mixture is not of concern because the powder is never to be taken internally. A specific dry dye is Red Driad Powder Paint (Nontoxic) manufactured by Binney & Smith, Inc. of Easton, Pennsylvania.

Using the indicator dye markings as a guide, the areas of occlusion on the prosthetic device can be corrected, as by grinding out the highlighted markings with a fissure or a round dental burr. Thereafter, the prosthetic device can be rinsed and blown dry, and the process of fitting repeated until undesired occlusions are eliminated and undesired tightness of the prosthetic device is minimized.

By using the inventive technique, an excellent fitting crown or like prosthetic device can be achieved, and a clean, unscratched and undamaged mounting, die or prepared tooth is maintained.

The invention has now be explained with reference to specific embodiments. Other embodiments will be apparent to workers familiar with the art of dentistry. For example the same technique may be used for fitting inlays or even bridge abutments. It is therefore not intended that the invention be limited, except as indicated by the appended claims.

What is claimed is:

1. A metod for indicating undesired occlusions between a first dental surface of a mounting and a second dental surface of a prosthetic device, said indicating being on said second dental surface, such that undesired occlusions can be eliminated, said method comprising the steps of:
   (a) applying a thin, uniform film of an adhesive liquid to said first dental surface;
   (b) abutting said first dental surface to said second dental surface, said second dental surface being substantially dry, thereby to transfer a residue of said liquid to points of occlusion between said first dental surface and said second dental surface;
   (c) removing said second dental surface from said first dental surface; and thereafter
   (d) highlighting said points of occlusion on said second dental surface by dusting said second dental surface with a colored powder in sufficient quantity to adhere to said residue on said second dental surface, whereby said points of occlusion are indicated.

2. A method according to claim 1 wherein said applying step comprises coating said first dental surface with a mixture of glycerin and soap, and blowing off any excess of said mixture in order to leave said thin, uniform film.

3. The method according to claim 1 or 2 wherein said highlighting step comprises dusting said second dental surface with a colored powder comprising a mixture of a dye powder and talcum powder, and blowing off any excess powder thereby to leave colored powder adherent only to points of occlusion indicated by said residue.

4. The method according to claim 1 or 2 further including thereafter the steps of:
   (e) grinding away said points of occlusion marked on said second dental surface having been highlighted by said colored powder on said second dental surface; and
   (f) repeating at least steps (b) through (e) in sequence until undesired occlusions between said first dental surface and said second dental surface have been eliminated and a substantially uniform fit is achieved between said mounting and said prosthetic device.

* * * * *